(12) United States Patent
Fadler et al.

(10) Patent No.: US 8,424,823 B2
(45) Date of Patent: Apr. 23, 2013

(54) STAND FOR IMAGING

(75) Inventors: Franz Fadler, Hetzles (DE); Paul Weidner, Pressath (DE); Satchi Panda, Fremont, CA (US)

(73) Assignee: Siemens Aktiengesellschaft, München (DE)

( * ) Notice: Subject to any disclaimer, the term of this patent is extended or adjusted under 35 U.S.C. 154(b) by 649 days.

(21) Appl. No.: 12/625,145

(22) Filed: Nov. 24, 2009

(65) Prior Publication Data

US 2010/0148021 A1    Jun. 17, 2010

(30) Foreign Application Priority Data

Nov. 27, 2008   (DE) .......................... 10 2008 059 344

(51) Int. Cl.
*F16M 13/00* (2006.01)

(52) U.S. Cl.
USPC ................ 248/288.31; 248/181.1; 248/282.1; 403/76

(58) Field of Classification Search ............. 248/288.31, 248/181.1, 181.2, 282.1, 663; 403/76, 90, 403/122, 124, 125, 126
See application file for complete search history.

(56) References Cited

U.S. PATENT DOCUMENTS

| | | | | |
|---|---|---|---|---|
| 3,888,534 A * | 6/1975 | Hall et al. | ...................... | 294/174 |
| 4,515,333 A * | 5/1985 | Pugh et al. | ............... | 248/123.11 |
| 5,790,307 A * | 8/1998 | Mick et al. | .................... | 359/382 |
| 6,651,347 B2 * | 11/2003 | Uhl | ................................. | 30/383 |
| 7,207,531 B2 * | 4/2007 | Piontkowski | .............. | 248/122.1 |
| 8,083,196 B2 * | 12/2011 | Chang | ........................ | 248/276.1 |

FOREIGN PATENT DOCUMENTS

| DE | 3520837 C1 | 10/1986 |
|---|---|---|
| DE | 69106701 T2 | 7/1995 |

OTHER PUBLICATIONS

German Office Action dated May 14, 2009 with English translation.

\* cited by examiner

*Primary Examiner* — Terrell McKinnon
*Assistant Examiner* — Steven Marsh
(74) *Attorney, Agent, or Firm* — Lempia Summerfield Katz LLC

(57) ABSTRACT

A stand, especially a floor stand, with a movable arm with an attachment section provided at the end of the arm for an object to be held by means of the stand, especially an imaging device in the form of an ultrasound head, with the attachment section being supported movably on the arm via a ball-and-socket joint comprising a ball head carrying the attachment section and a head holder supporting the ball head on the arm side, with a locking device being provided for releasable locking of the ball head (32) in its adopted position in the head holder.

18 Claims, 2 Drawing Sheets

STAND FOR IMAGING

This application claims the benefit of DE 10 2008 059 344.3 filed Nov. 27, 2008, which is hereby incorporated by reference.

BACKGROUND

The present embodiments relate to a stand with a movable arm and an attachment section provided on the end of the arm for an object to be held by the stand.

Stands are frequently used with a medical imaging apparatus, such as an ultrasound head, and have a movable arm arranged on a vertical pillar on which the imaging apparatus is arranged. The movement capability for the ultrasound head is provided by the movability of the arm and also by a ball-and-socket joint support of the imaging apparatus on the arm. In practice, the imaging apparatus, for example the ultrasound head (the imaging apparatus is to be taken as including larger systems or components, for example, including a frame or the like), is applied and positioned by the doctor on a patient, for example, to record an image of a breast in a mammography. The doctor aligns the ultrasound head depending on the position of the breast in order to position the ultrasound head correctly relative to the breast or relative to a specific point (e.g., the nipple). The doctor records images of the entire desired area under investigation from which, for example, 3D images will subsequently be reconstructed. The ability to move the ultrasound head into a given position depending on the position or the size of the breast is made possible by the movability of the arm and especially the ball-and-socket joint support of the imaging apparatus.

During mammography, the doctor may apply considerable pressure and maintain this pressure on the ultrasound head while recording the images. Considerable pressure is applied to the breast during this process. When an ultrasound image recording apparatus including a stand is used, the patient is lying so that the ultrasound head can be applied and pushed on by the doctor from above and slightly inclined to the side. The doctor may press the ultrasound head during the entire imaging process with considerable pressure against the breast; this requires great effort on the part of the doctor and results in the problem that the ultrasound head moves around the ball-and-socket joint support, either as a result of the breathing movement of the patient or the movement of the doctor. Such a change in the relative position of the ultrasound head to the imaging area has a negative effect on the quality of the images recorded.

SUMMARY AND DESCRIPTION

The present embodiments may obviate one or more of the drawbacks or limitations in the related art. For example, in one embodiment, a stand may improve image recording.

In one embodiment, the stand may include a locking device for releasably locking a ball joint head once the ball joint head has adopted a specific position in a head support.

In one embodiment, the stand may allow, as a result of the ball-and-socket joint support of the imaging device, an accurate and precise alignment of the ultrasound head relative to the imaging area, and provide, as a result of the ability to lock any given position of the ultrasound head adopted relative to the arm, a system for fixing this optimum position for the subsequent imaging. Accordingly, the doctor merely needs to exert the required pressure against the body under investigation. There is no longer any danger of the relative position of the ultrasound head being changed by a movement of the ball joint, since this movable link is fixed or locked using the locking device of one of the present embodiments. Accordingly, the alignment during imaging is no longer changeable.

The locking device may include or is a clamping device, which clamps the ball head into the head support. Once a user (e.g., the doctor) has made the alignment, the user merely actuates the locking device, which directly results in the clamping of the movable parts in relation to each other, thereby fixing the alignment. For clamp locking, the locking device may include a clamping element able to be moved linearly via a motorized positioning element that, on actuation of the positioning element, is able to be moved against the ball head, pressing the ball head against the head support. The use of a motorized adjustment element for moving the clamping element allows an automated locking. The doctor only has to give a corresponding electrical actuation signal to the locking device or to the motorized adjustment element (e.g., through a suitable control key that the user holds, or the like in the area of the imaging device), in order to control an adjusting motor, which then moves the clamping element into the clamping position. The clamping element may be a clamping sleeve and may include a pressure surface adapted to the shape of the ball head, which presses against and clamps the ball head. This enables a large clamping surface to be realized, which makes clamping that is secure, by virtue of being a high-force and a form-fit clamping, possible.

The motorized adjustment element may be an electric motor with a downstream transmission. The transmission may be coupled directly or indirectly to the clamping element via a shaft. A suitable gearing can be set by the transmission so that the clamping can be realized accurately and precisely and with high clamping pressure. The shaft may include an outer thread, on which runs a sleeve or nut provided with an inner thread. The sleeve or nut is moved along as the shaft turns and is supported on or connected to the clamping element. The inner thread and the outer thread may be trapezoidal threads with a small pitch. Thus, clamping involves actuating the electric motor to turn the shaft via the transmission, which moves the sleeve or nut that runs on the outer thread of the shaft quasi axially, moving the clamping element, to which the sleeve or nut is connected or coupled, against the ball head and clamping the ball head. For fixing or supporting the sleeve or nut, a recess is provided on the clamping element, in which the sleeve or nut is preferably loosely located. A loose location is sufficient since when the strain is relieved on the sleeve or on the nut (e.g., when the shaft is turned back via the electric motor), the clamping connection is automatically removed and the ability to rotate is re-established.

In one embodiment, the clamping element may be held pre-tensioned via at least one tensioning element (e.g., a coil spring) against the ball head. In other words, even when the strain on the clamping element is removed and there is no clamping, the clamping element may be in slight contact with the ball head, allowing the ball head to move but preventing movement of the clamping element that could lead to noises. In one embodiment, the sleeve or nut may loosely engage the clamping element or the clamping sleeve, respectively.

In one embodiment, for secure guidance of the clamping element, which is to be guided axially on the arm or the arm section respectively in which the components for movement and clamping are contained, the clamping element may be guided linearly on one or more guide pins, which extend between a fixed-position holder and the clamping element. The coil spring may be arranged around the guide pin to provide guidance and pre-tensioning as well.

The ball-and-socket joint support allows any given rotation or pivoting of the imaging device relative to the arm. Since various connecting lines are routed via the arm to the imaging device, one embodiment may include a limiting stop to limit the rotational movement of the ball head in the head support so that the ball head cannot simply be rotated through 360° any number of times. Such a limiting stop may, for example, be set at an angle of rotation of approximately 290°. Any other maximum angles of rotation (e.g., 320°) may be realized via the limiting stop.

In one embodiment, the limiting stop may include a stop element provided on a propeller shaft joint or a propeller shaft arranged on the ball head, which is supported with a second end on the clamping element. The propeller shaft joint or the propeller shaft may include one or more stops limiting the rotational movement. The propeller shaft joint or the propeller shaft is linked to the clamp element to allow free movement. In one embodiment, the stop element located on the propeller shaft joint or the propeller shaft may be a laterally-protruding pin that comes into contact, on sufficient pivoting, with one or more stops limiting the rotary movement, which may be arranged on the clamping element.

In addition to such a rotational movement limiting stop, one embodiment may include a limiting stop of the pivoting movement of the ball head in the head support. The limiting stop of the pivoting movement may limit a pivot angle, (e.g., a maximum of 90° or larger or smaller maximum pivot angles). This pivot limiting may be formed by a free edge of the head support (i.e. the free edge of the head support forms the limiting stop of the pivoting movement), with which an extension provided on the ball head comes into contact.

DETAILED DESCRIPTION

Figure 1:
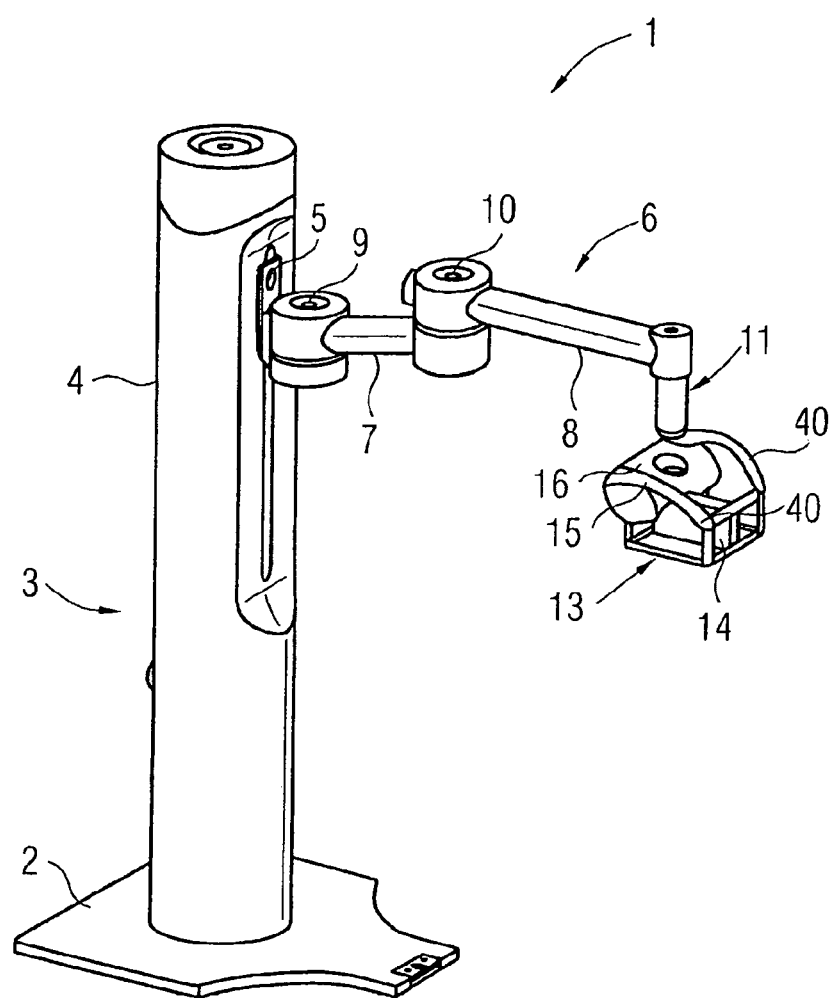
FIG. 1 shows one embodiment of a stand.
Figure 2:
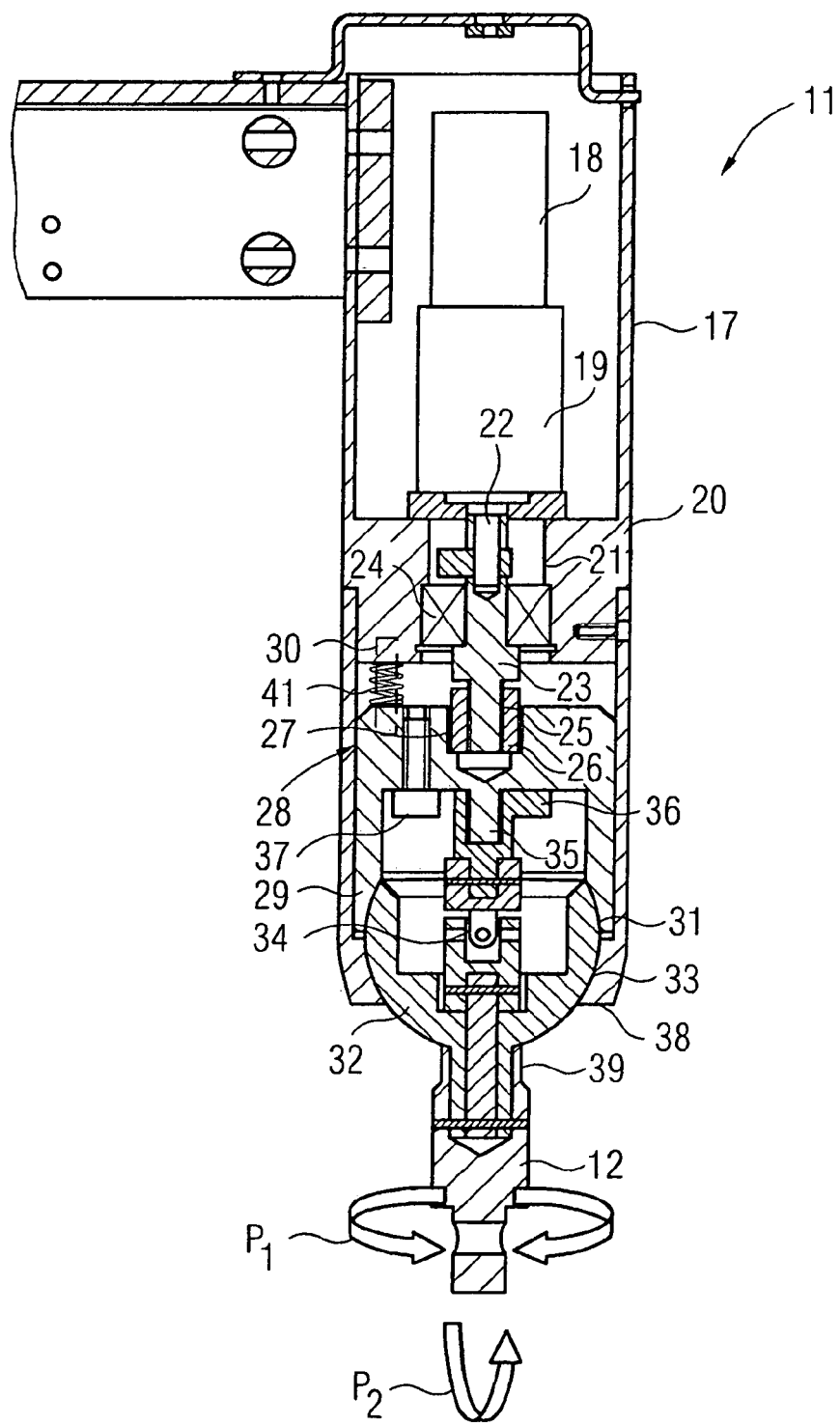
FIG. 2 shows an enlarged sectional view of one embodiment of a stand.

FIG. 1 shows an embodiment of a stand 1 with a floor plate 2, on which a vertical pillar 3 with a casing 4 is arranged. Guided vertically on the vertical pillar 3 via a linear guide (e.g., rail and guide carriage) to allow a vertical movement is an arm 6 comprising two arm sections 7, 8. The arm 6 is pivotable via a first pivot 9 relative to the linear guide 5. A second pivot point 10 between the arm sections 7 and 8 allows the two arm sections 7 and 8 to pivot relative to one another. An adapter 11, on which an attachment section shown in FIG. 2 is provided, is located at an end of the arm section 8. An imaging device 13, (e.g., an ultrasound head 14 for recording ultrasound images during the course of a mammography) can be detachably fastened to the adapter 11. The imaging device 13 may include a frame-type housing 15, on which a section 16 with diverse operating devices (e.g., pivot motor, control system) is provided, and the pivotable ultrasound head 14. The imaging device 13 can be attached to the attachment section 12 of the arm 6, which allows the imaging device 13 to be rotated and pivoted in order to enable the imaging device 13 to be aligned in relation to the breast to be imaged during the mammography. During a mammography, the alignment is usually undertaken such that the ultrasound head is aligned relative to a fixed point on the breast, usually the nipple, so that the ultrasound head lies above the fixed point. For imaging, the ultrasound head is then moved via an imaging device-side movement system, starting from the fixed point, to the respective sides, to record an ultrasound image of the breast.

FIG. 2 shows an enlarged sectional view through the adapter 11. The adapter 11 includes a housing 17, which may include a motorized control element in the form of an electric motor 18 with a downstream transmission 19. The transmission 19 is supported on a housing-side holder 20, which includes a central breakthrough 21 into which a take-off shaft 22 engages a shaft 23, which is rotationally supported via a suitable bearing 24 in the holder 20. The shaft 23 features an outer thread 25 (e.g., a trapezoidal thread), on which a sleeve 26 with an inner thread runs. The sleeve 26 is loosely located in a recess 27 of a clamping element 28. The clamping element may be a clamping sleeve 29. The clamping sleeve 29 is able to be moved axially in the housing 17. In other words, the clamping sleeve can be displaced in the direction of the housing longitudinal axis, for which purpose the electric motor 18 and the downstream transmission 19 is used. For guidance of this linear movement two guide pins 30 (of which only one is shown), which extend between the holder 20 and the clamping sleeve 29, are provided.

The clamping sleeve 29 has a curved clamping surface 31 on a lower free annular edge, the shape of which corresponds to an outer side of a ball head 32 that is arranged movably in a head support 33 of the housing 17. In other words, the ball head 32 and the head support 33 form a ball-and-socket joint. The attachment section 12 is located on the ball head 32 and may be attached to the imaging device 13. The ball head 32 is loosely connected, via a propeller shaft 34, to the clamping sleeve 29 with a retaining pin 35. In other words, the clamping sleeve 29 is movable relative to the propeller shaft 34.

As shown in FIG. 2, as indicated by the double-headed arrow, the attachment section 12 can be turned in the head support 33 via the ball head 32. The ball head 32 can also be pivoted in the head support, as is shown by the arrow P2. To limit the angle of torsion (P1), a stop element 36 is provided on the propeller shaft and a stop 37 is provided on the clamping sleeve 29 in the form of a stop screw, which delimits the rotational movement. As a result of the use of the propeller shaft 34, since the horizontal relative position of the stop element 36 in relation to the vertical axis and of the stop 37 does not change even if the ball head 32 is pivoted in the direction P2, there is always a movement limitation independent of the ball head position. The rotational movement may be limited to 290° as the maximum angle of rotation. The pivoting movement may be limited to 90° as the maximum pivot angle.

To limit the pivoting (P2), a lower edge 38 of the head support 33 forms the stop for a corresponding stop projection 39 of the ball head.

To record an image, the user now initially positions the imaging device 13, by grasping the imaging device 13 with his hand by the two bars 40 shown in FIG. 1, whereby the arm 6 can be moved vertically and can be pivoted around the corresponding ball joint 9, 10, and the imaging device 13 can also be pivoted around the ball-and-socket joint connection (i.e., ball head 32, ball support 33). In order to now be able to lock this pivot position, one embodiment of the locking system described above is used, including the electric motor 18, the downstream transmission 19, the movement mechanism connected to the downstream transmission, as well as the clamping sleeve 29. The clamping sleeve 29 is located in the initial position if the ball head 32 can thus be moved relative to the head support 33, in a position released from the ball head 32 (i.e., not clamped rigidly against the head 32). The clamping sleeve 29 is pre-tensioned, via coil springs 41, which are arranged around the guide pins 30, against the ball head 32, and rest in the released position lightly against the ball head 32 without restricting the movement of the ball head 32.

If a pivoting or rotational position adopted is now to be locked, the user may issue an electrical signal to the electric motor 18 via a button, which may be a bar 40, provided on the imaging device 13. The control motor 18 turns the shaft 23 via the transmission 19. As a result of the shaft transmission, the sleeve 26 moves downwards on the shaft 23, as can be seen in FIG. 2. Thus, the sleeve 26 is moved against the clamping sleeve 29, which is pressed downwards with a rounded clamping surface 31 against an outer surface of the ball head 32. The ball head 32 will be pressed against the head support 33 and clamped in position as a result. The pressing-on process is movement-controlled (e.g., by recording the rotation of the output shaft 22) or force controlled (e.g., via a sensor measuring the press-on force), so that there is no resulting overload.

If the locking is to be released again via the head clamping, the electric motor 18 is activated again and operates in the other direction. In other words, the shaft 23 will be moved via the transmission 19 in the opposite direction. This leads to the sleeve 26 moving in the other direction on the outer thread 25 of the shaft 23, and the sleeve 26 is "pulled out" of the recess 27. This relieves the strain on the clamping sleeve 29. The clamping sleeve 29 is simultaneously slightly pre-tensioned against the ball head 32 via the two or more coil springs 41. The ball head 32 is thus released again.

The sleeve 26 and the propeller shaft 34 are both loosely supported on the clamping sleeve 29, the sleeve in the recess 27 and the propeller shaft 34 on the retaining pin 35. This loose support ensures the axial movability of the clamping sleeve 29.

The relative position of the imaging facility 13 can be fixed in any number of given rotational or pivot positions with the embodiments described above.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A stand comprising:
   a movable arm;
   an attachment section provided at an end of the movable arm for an object to be held by the stand; and
   a ball-and-socket joint movably coupling the attachment section to the movable arm, the ball-and-socket joint comprising a ball head carrying the attachment section and a head holder supporting the ball head,
   wherein the head holder comprises a locking device for releasable locking of the ball head in an adopted position in the head holder,
   wherein the locking device comprises a clamping device operable to clamp the ball head in the head holder, and
   wherein the locking device further comprises a clamping element linearly movable against the ball head upon actuation of a motorized control element, pressing the ball head against the head holder.

2. The stand as claimed in claim 1, wherein the clamping element comprises a clamping sleeve, the clamping sleeve comprising a pressure surface adapted to the shape of the ball head, the pressure surface pressing against and clamping the ball head.

3. The stand as claimed in claim 1, wherein the motorized control element comprises an electric motor with a downstream transmission coupled to the clamping element via a shaft.

4. The stand as claimed in claim 3, wherein the shaft further comprises an outer thread, on which a sleeve or a nut provided with an inner thread moves along as the shaft turns, and
   wherein the sleeve or the nut is supported on or connected to the clamping element.

5. The stand as claimed in claim 4, wherein a recess is provided on the clamping element to loosely house the sleeve or the nut.

6. The stand as claimed in claim 1, wherein the clamping element is pre-tensioned with at least one tensioning element in contact with the ball head.

7. The stand as claimed in claim 1, wherein the clamping element is guided linearly on a guide pin that extends between a fixed-position holder and the clamping element.

8. The stand as claimed in claim 6, wherein the at least one tensioning element is arranged around a guide pin.

9. The stand as claimed in claim 1, further comprising a limiting stop operable to limit a rotational movement of the ball head in the head holder.

10. The stand as claimed in claim 9, further comprising a propeller shaft that is supported on the clamping element,
    wherein a stop element is provided on a propeller shaft link or the propeller shaft, and
    wherein one or more stops are provided on the clamping element, the one or more stops operable to restrict the rotational movement.

11. The stand as claimed in claim 1, further comprising a limiting stop operable to restrict a pivoting movement of the ball head in the head holder.

12. The stand as claimed in claim 11, wherein the limiting stop is formed by a lower free edge of the head holder, which comes into contact with a projection on the ball head.

13. The stand as claimed in claim 1, further comprising a limiting stop operable to limit a rotational movement of the ball head in the head holder.

14. The stand as claimed in claim 2, wherein the motorized control element comprises an electric motor with a downstream transmission coupled to the clamping element via a shaft.

15. The stand as claimed in claim 5, wherein the clamping element is pre-tensioned with at least one tensioning element in contact with the ball head.

16. The stand as claimed in claim 6, wherein the clamping element is guided linearly on a guide pin that extends between a fixed-position holder and the clamping element.

17. The stand as claimed in claim 2, further comprising a limiting stop operable to limit a rotational movement of the ball head in the head holder.

18. The stand as claimed in claim 8, further comprising a limiting stop operable to restrict a pivoting movement of the ball head in the head holder.

* * * * *